(12) United States Patent
Alexander

(10) Patent No.: US 6,398,790 B1
(45) Date of Patent: Jun. 4, 2002

(54) DELIVERY ASSISTANCE DEVICE

(75) Inventor: Gary Alexander, Baton Rouge, LA (US)

(73) Assignee: Medisys Technologies, Inc., Baton Rouge, LA (US)

( * ) Notice: Subject to any disclaimer, the term of this patent is extended or adjusted under 35 U.S.C. 154(b) by 0 days.

(21) Appl. No.: 09/849,094

(22) Filed: May 4, 2001

(51) Int. Cl.⁷ .............................................. A61B 17/42
(52) U.S. Cl. ........................ 606/122; 606/119; 606/121
(58) Field of Search .............................. 606/122, 123, 606/119, 106, 127, 124, 121; 604/74, 149

(56) References Cited

U.S. PATENT DOCUMENTS

| | | | |
|---|---|---|---|
| 13,453 A | | 8/1855 | Buffum |
| 713,166 A | * | 11/1902 | St. Cyr |
| 1,690,942 A | | 2/1928 | Odell |
| 1,782,814 A | | 11/1930 | Froehlich |
| 2,618,272 A | | 2/1952 | Larson |
| 3,139,886 A | | 7/1964 | Tallman et al. |
| 3,550,595 A | | 12/1970 | Laufe |
| 3,605,748 A | | 9/1971 | Salinas-Benavides |
| 3,665,925 A | | 5/1972 | Dersookian |
| 3,785,381 A | | 1/1974 | Lower et al. |
| 3,789,849 A | | 2/1974 | Laufe et al. |
| 3,794,044 A | | 2/1974 | Vennard et al. |
| 4,597,391 A | * | 7/1986 | Janko |
| 4,875,482 A | | 10/1989 | Hariri et al. |
| 5,122,148 A | | 6/1992 | Alexander |
| 5,207,687 A | * | 5/1993 | Bernon |
| 5,217,467 A | * | 6/1993 | Alexander |
| 5,318,573 A | | 6/1994 | Alexander |
| 5,593,413 A | | 1/1997 | Alexander |
| 5,632,750 A | | 5/1997 | Alexander et al. |

FOREIGN PATENT DOCUMENTS

| | | |
|---|---|---|
| AU | B-22271/92 | 5/1996 |
| DE | 2233840 | 1/1974 |
| DE | 2925386 | 1/1981 |

OTHER PUBLICATIONS

PCT/FR89/00252 WO89/11253, Nov. 30, 1989, Bernon, France, (Abstract Only).

* cited by examiner

*Primary Examiner*—Pedro Philogene
(74) *Attorney, Agent, or Firm*—Roy, Kiesel, Keegan & DeNicola

(57) ABSTRACT

A device for assisting childbirth, preferably made of separate sheets of loosely knitted polypropylene loops. Each sheet has a control end, an opposite mouth end, and a pair of insertion arms attached to the edges of the sheets. The insertion arms of each sheet slidingly engage one another. Thus, one sheet may be inserted between the fetal head and the birth canal wall until it is properly placed about the fetal head. The second sheet can then engage the first sheet, sliding into position around the fetal head as well, thereby forming an elongated gripping member completely encircling the fetal head. A drawstring may be provided to assist in initiating traction. Thereafter, pulling on the gripping member will cause the loops to lengthen longitudinally and compress in their transverse dimension, causing the circumference of the gripping member to decrease and thereby grip the fetal head.

19 Claims, 8 Drawing Sheets

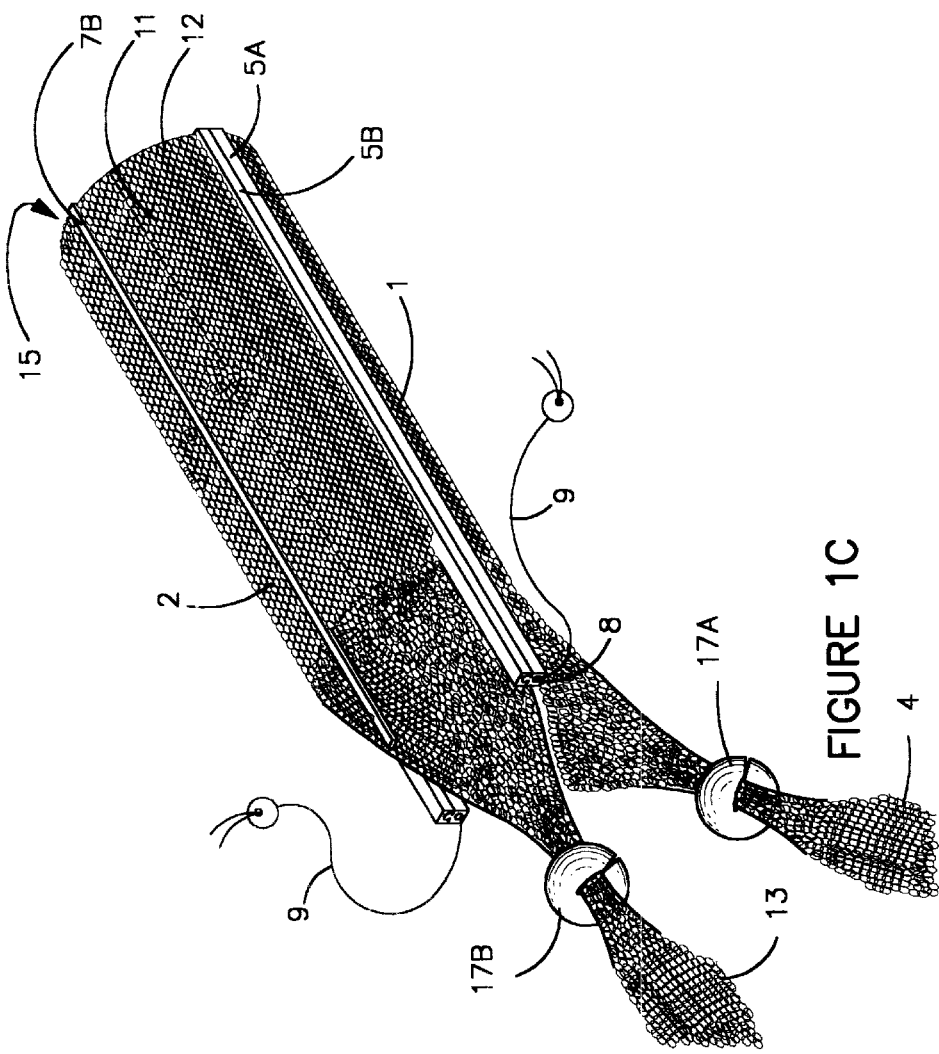

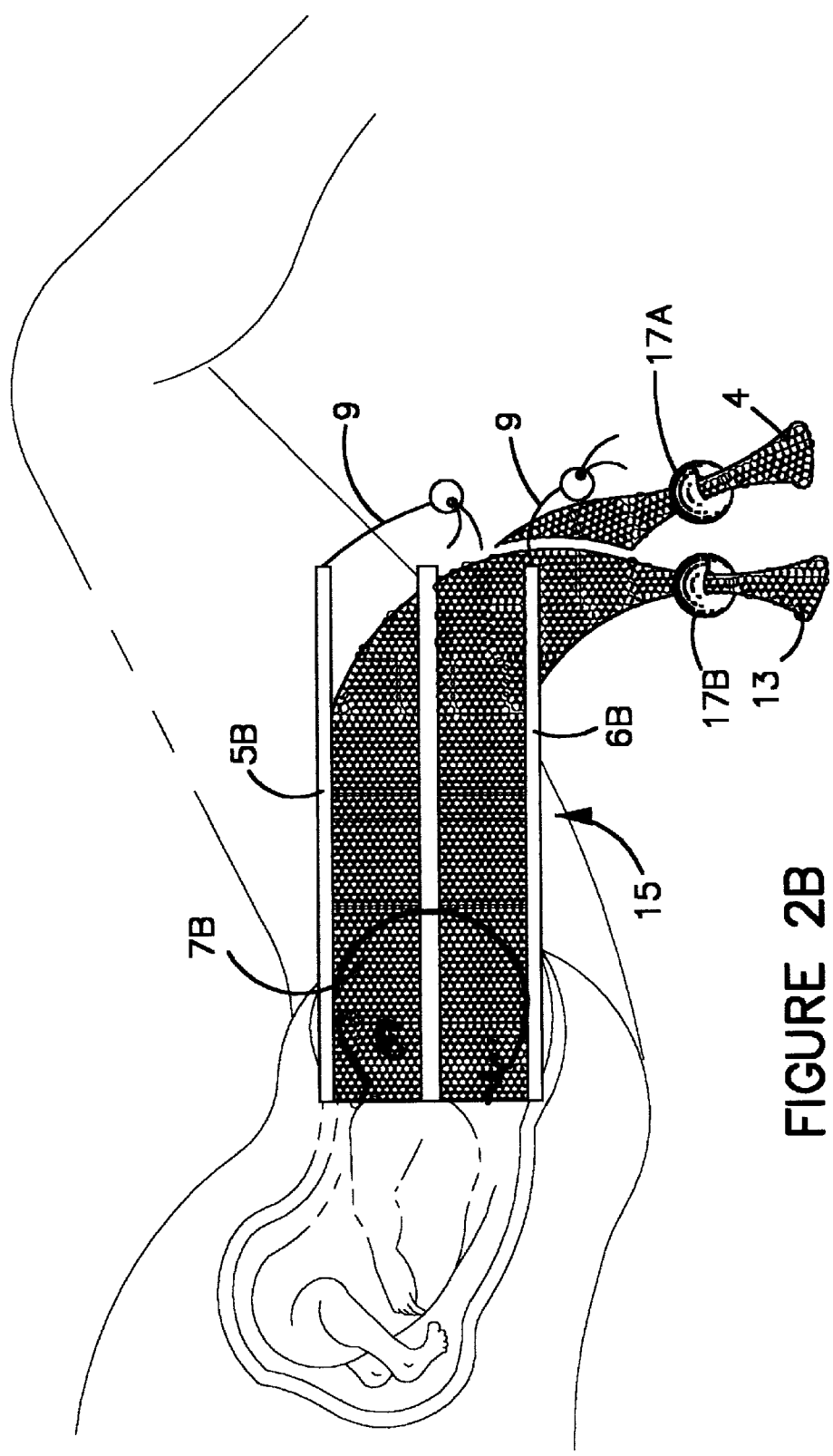

DELIVERY ASSISTANCE DEVICE

BACKGROUND OF THE INVENTION

1. Field of the Invention

The invention relates to obstetrical devices in general and to devices for assisting delivery of a human fetus in particular.

2. Prior Art

The principle delivery assistance device in the prior art are forceps. Forceps generally comprise a pair of opposed metal arms that are separately placed on either side of the fetus's head. Once the arms are in place, they are typically joined together at a centrally located hinge so that inward pressure on the control end of the two arms will result in the inward movement of the gripping ends of the arms against the fetus's head. Through this gripping, traction is obtained with the fetus's head, and by exerting lateral force against the forceps, the fetus may be extracted from the birth canal.

Several problems can arise in the use of the forceps. When properly applied, the gripping end of the forceps are positioned over the upper jaw bone of the fetus in line with the ear. However, properly placing the forceps can be difficult. Frequently, only the top of the fetus's head is visible in the birth canal when the forceps are applied. Particularly when the fetus is not properly positioned in a face down position in the birth canal, it can be difficult for the physician or other medical professional to locate the appropriate place on the fetus to position the forceps. Thus, instead of the bones of the upper jaw, the forceps may be placed against the nose, eye, temple, or other inappropriate portion of the fetus's head. When the forceps are tightened, pressure is exerted against this fetus's head with the gripping points of the forceps. If these points are positioned improperly, pressure may be exerted on an eye, an ear, a temple, or other portions of the fetus's head which may be injured or deformed under such pressure, and in fact such injuries are all too common in forceps assisted deliveries.

One delivery assistance device that attempts to address this problem is the sock-like axial gripping delivery assistance device such as that illustrated in U.S. Pat. No. 5,910,146 (the '146 Patent) which is hereby incorporated by reference in its entirety. These devices use an elongated hollow member comprised of a plurality of fibers loosely woven together and having an open mouth. In operation, the open mouth of delivery assistance devices such as that disclosed in the '146 Patent will be placed over the head of the fetus. When the physician pulls on the end of the tube opposite the fetus, the fibers will tighten and axially grip the head of the fetus, much like the way that the novelty item, "Chinese finger cuffs," grip the fingers of a user. Unlike forceps, such gripping will be spread out across the fall surface area of the fetus's head, rather than being concentrated in two points. By spreading the gripping force out across the entire fetal head, the risk of injury or deformation is greatly reduced.

Delivery assistance devices such as that disclosed in the '146 Patent work very well once they are inserted over the fetal head. However, positioning the device over the fetal head can be problematic. When a delivery assistance device of any type is needed, the fetus has usually descended into the birth canal, but is not moving forward or is not moving forward fast enough. Unless a breach birth is underway, the fetus will be positioned head first in the birth canal, which will be pressed tightly around the head so that only a small circle at the top of the fetal head is exposed. Forcing a woven sock-like member between the fetal head and the birth canal walls can be difficult, as the loose edges of the elongated hollow sock-like member tend to gather at the boundary between the fetal head and the birth canal. This can prevent the mouth of the delivery device from being placed completely over the fetus's head, making the initiation of axial gripping and traction difficult. Therefore, what is needed is a delivery assistance device that meets the following objectives.

OBJECTS OF THE INVENTION

It is an object of the invention to provide a device capable of assisting in the delivery of a fetus.

It is another object of the invention to provide a device capable of gripping the head of a fetus and distributing that gripping pressure evenly across the fetal head.

It is another object of the invention to provide a device for assisting in the delivery of a fetus that will reduce or eliminate the injuries inherent in forceps or vacuum type assisted delivery systems.

It is still another object of the invention to provide a device for assisting in the delivery of a fetus that may be quickly and easily placed over the head of the fetus by the physician or other medical professional, and quickly and easily removed if necessary.

Still other objects and advantages of the invention will become apparent from the following description of the invention.

SUMMARY OF THE INVENTION

The invention comprises an elongated gripping member for assisting in the delivery of a fetus. Although the invention is described in terms of a human fetus, it is to be understood that the invention is equally applicable to non-human fetuses, and that it may be used in the delivery of the same. The elongated gripping member is made up of two separate sheets of loosely knitted fibers, preferably interlocking loops of polypropylene or nylon monofilament. Each sheet has a control end and a mouth end opposite the control end and a pair of insertion arms attached to each end of the sheets. Located between the insertion arms is a central insertion arm. The outside insertion arms of each sheet will slidingly engage one another. Thus, one half of the elongated gripping member may be inserted between the fetal head and the birth canal wall until the first half is properly placed around the fetal head. The second half of the elongated gripping member can then engage the first half and slide into position around the fetal head as well, thereby forming the elongated gripping member in place to engage the fetal head. A drawstring is provided in one half of the elongated gripping member to allow the mouth of the gripping member to tighten slightly before traction is initiated. This will prevent the elongated gripping member from slipping until compression gripping is initiated. Once compression gripping is commenced, tension on the drawstring will no longer be required. Additionally, pressure on the fetal head will be uniformly distributed by the elongated gripping member, thereby reducing the likelihood of injury to or deformation of the fetus.

BRIEF DESCRIPTION OF THE DRAWINGS

FIG. 1C is a perspective view of a first sheet and second sheet fully engaged with the first sheet and forming an elongated gripping member.

FIG. 2B is a side cut-away view of an elongated gripping member formed of a first sheet fully engaged with a second sheet and fully enclosing the head of a fetus.

DETAILED DESCRIPTION OF THE BEST MODE

Figure 1A:
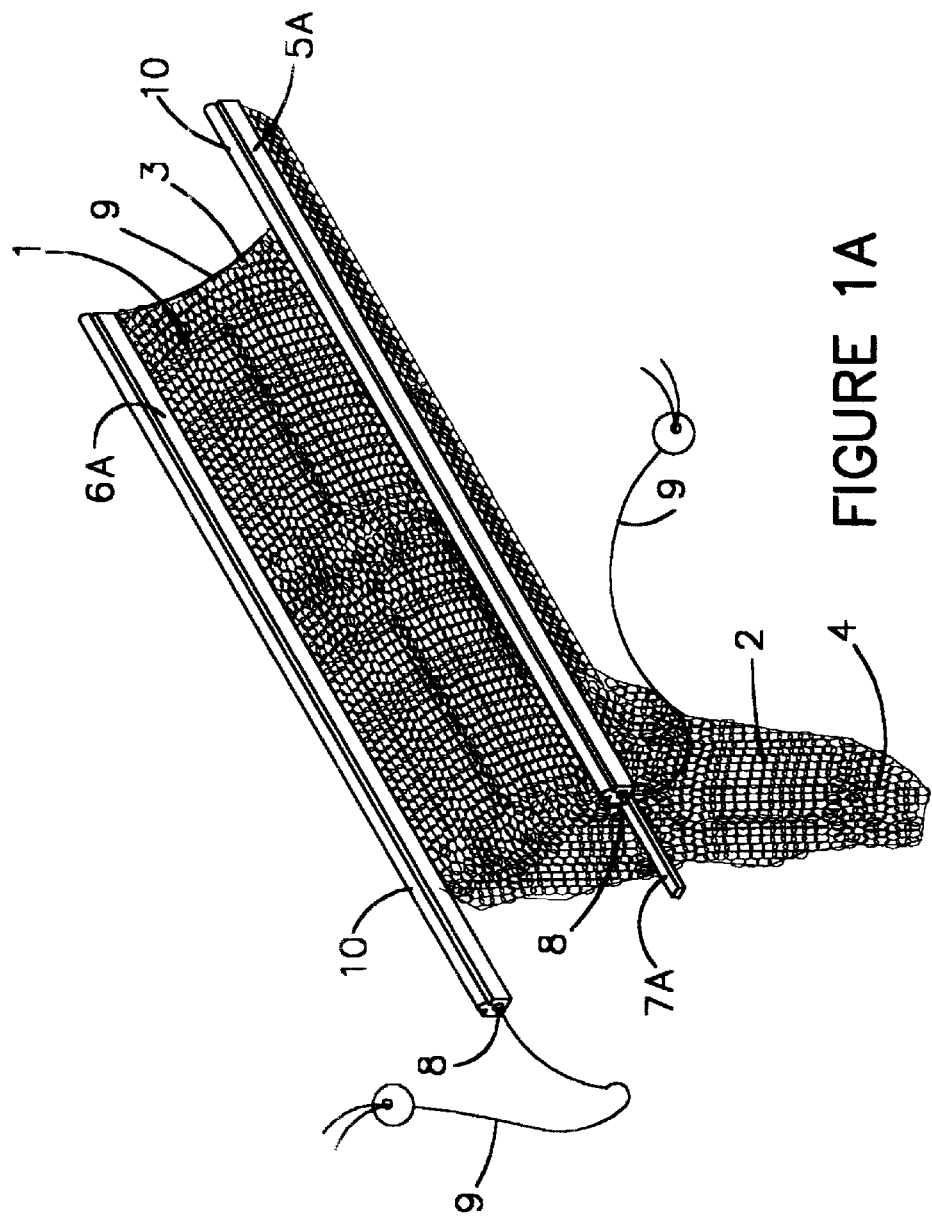
FIG. 1A is a perspective view of a first sheet.
Figure 1B:
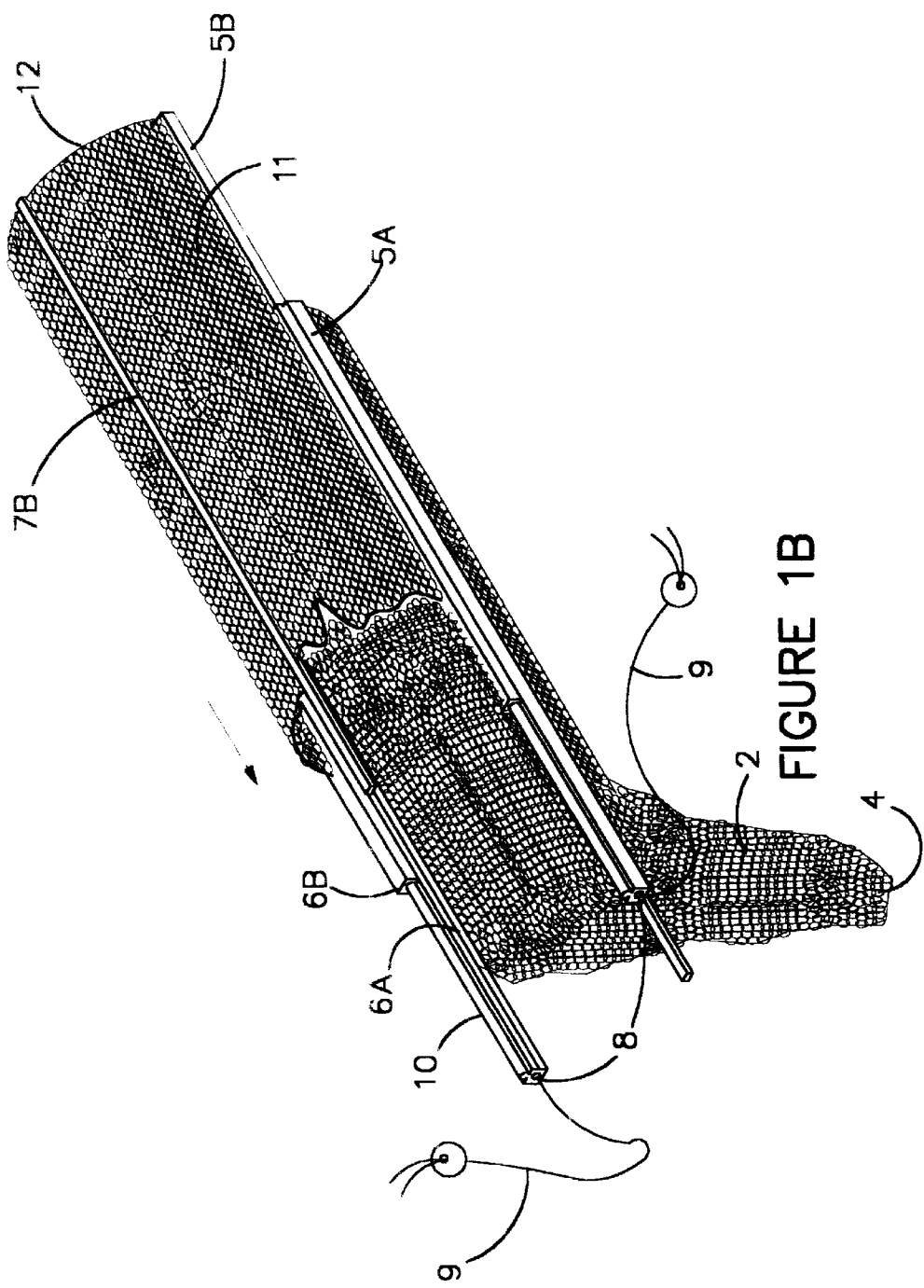
FIG. 1B is a perspective view of a first sheet and a partial cut-away view of a second sheet partially engaged with the first sheet.
Figure 2A:
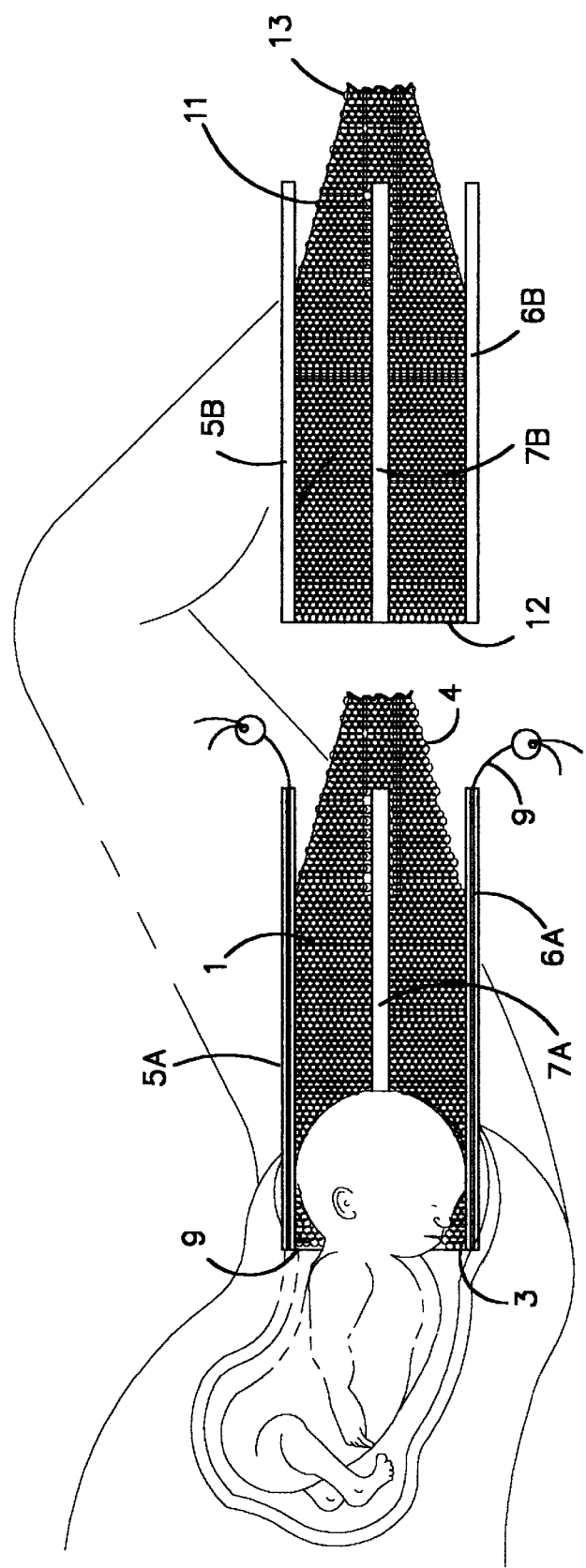
FIG. 2A is a side cut-away view of a first sheet fully positioned over the head of a fetus in the birth canal with a second sheet aligned to engage the first sheet.
Figure 2C:
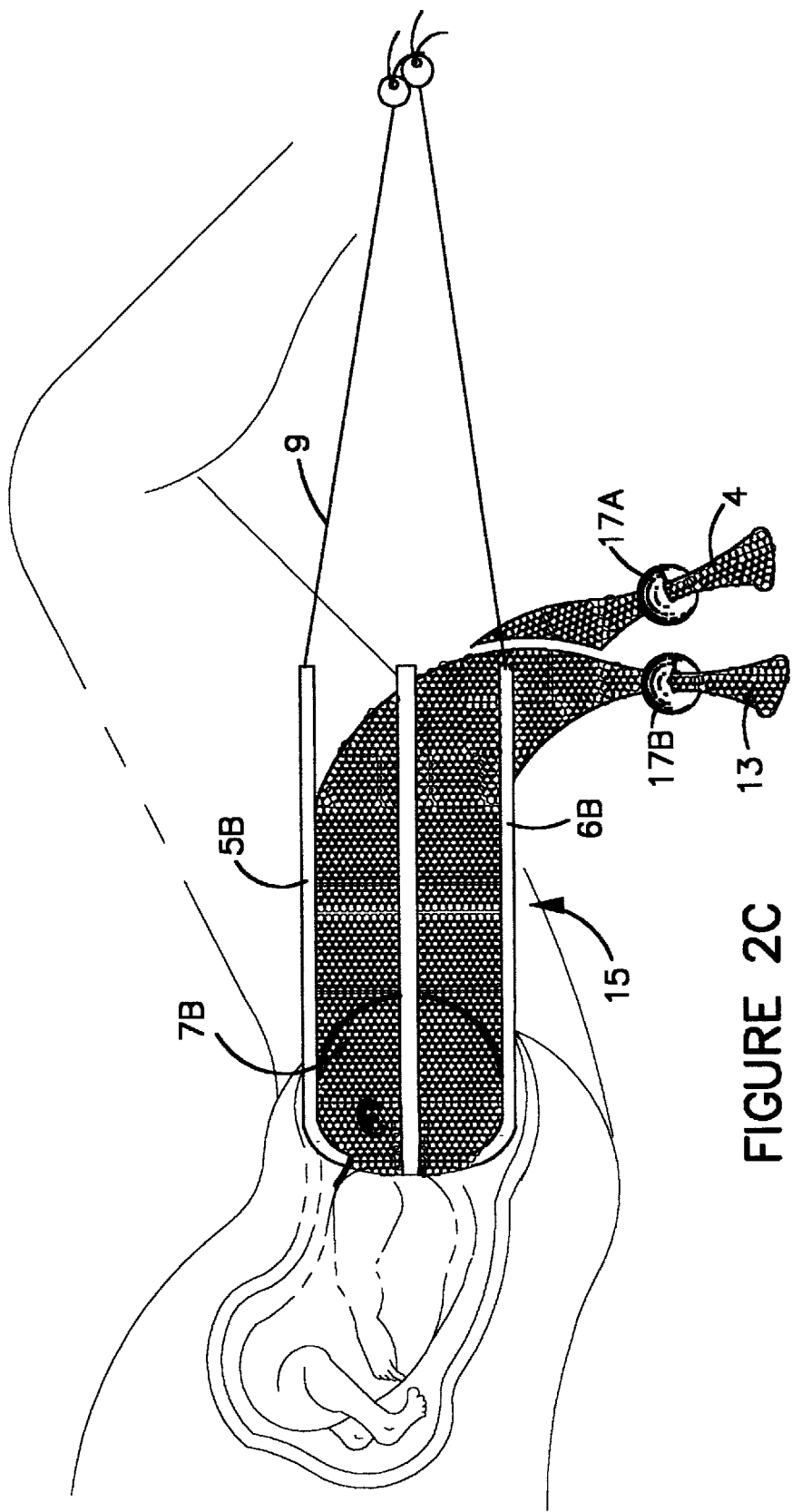
FIG. 2C is a side cut-away view of an elongated gripping member formed of a first sheet fully engaged with a second sheet and filly enclosing the head of a fetus and with the drawstring tightened to allow the initiation of compression gripping.
Figure 2D:
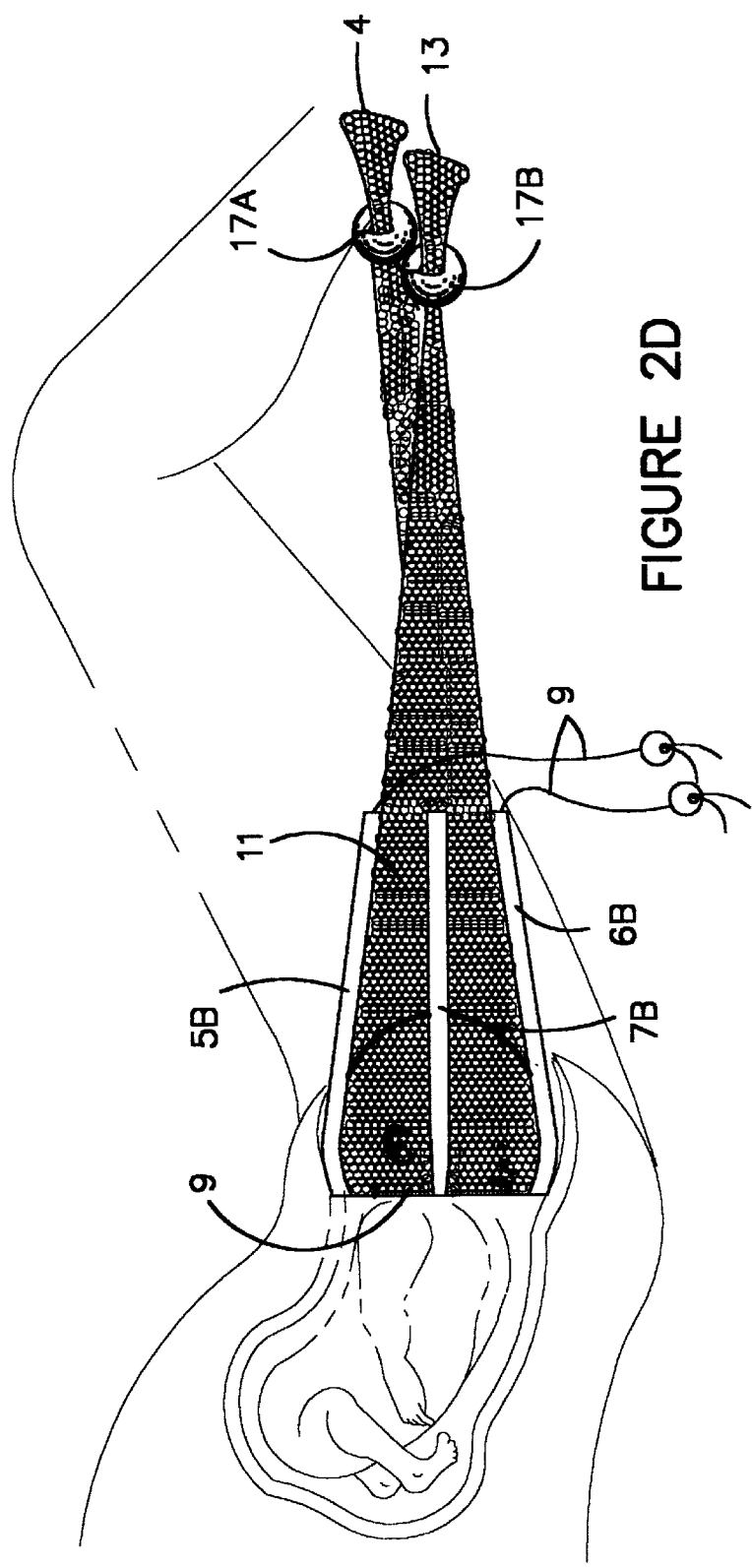
FIG. 2D is a side cut-away view of an elongated gripping member formed of a first sheet fully engaged with a second sheet and fully enclosing the head of a fetus and with traction being exerted against the fetus with the elongated gripping member.
Figure 5:
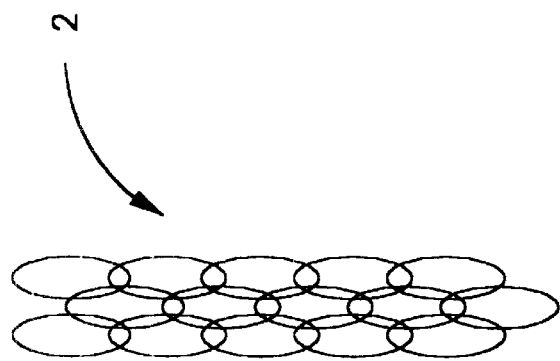
FIG. 5 is close side view of the fibers of the elongated gripping member illustrated in FIG. 4, during compression gripping.
Figure 4:
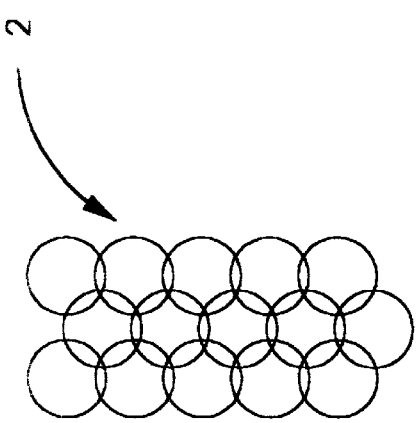
FIG. 4 is a close-up side view of the fibers of the elongated gripping member in a preferred jersey knit pattern.

The invention comprises an elongated first sheet 1 of loosely knitted fibers 2, preferably polypropylene monofilament or nylon. In a most preferred embodiment, fibers 2 are knitted together in series of interlocking loops as in a jersey knit. First sheet 1 has a mouth end 3 and a control end 4 opposite mouth end 3.

First sheet 1 extends between a first pair of insertion arms 5A, 6A which run from mouth end 3 toward control end 4. First insertion arms 5A and 6A should be thin and flexible in the dimensions transverse to the longitudinal dimension of first insertion arms 5A, 6A. However, first insertion arms 5A and 6A should be relatively stiff and strong in the dimension parallel to their longitudinal dimension. Preferably, first insertion arms 5A and 6A should be made of polystyrene.

A first central insertion arm 7A is positioned on first sheet 1 between first insertions arms 5A and 6A and also extends from mouth end 3 toward control end 4. Like first insertion arms 5A and 6A, first central insertion arm 7A should also be thin and flexible in the dimensions transverse to its longitudinal dimension and relatively stiff and strong in the dimension parallel to its longitudinal dimension. Preferably, first central insertion arm 7A should be made of polystyrene.

At least one of first insertion arms 5A or 6A should preferably contain a hollow channel 8 running through the length of first insertion arm 5A or 6A. In a preferred embodiment, a hollow channel 8 is contained in both first insertion arms 5A and 6A. Hollow channel 8 is to accommodate one or more drawstrings 9 running along mouth end 3 of first sheet 1. Drawstring 9 should be slidably attached to first sheet 1 at mouth end 3. This may be accomplished in any conventional manner, including running drawstring 9 through the fibers that make up first sheet 1 or by folding first sheet 1 over on itself to create a hem at mouth end 3 through which drawstring 9 may be disposed.

Drawstring 9 will preferably either be attached to one of first insertion arms 5A or 6A, will run along mouth end 3 of first sheet 1, and will run through hollow channel 8 and extend from hollow channel 8 at the end of one of the first insertion arms 5A or 6A adjacent to control end 4 of first sheet 1 or will run through both hollow channels 8 in each of first insertion arms 5A and 6A and along mouth end 3 of first sheet 1.

First insertion arms 5A and 6A will also preferably be provided with a male locking member 10 extending along the length of each insertion arm 5A and 6A. As will become apparent, instead of male locking member 10, first insertion arms 5A and 6A could just as easily be provided with female locking member 14, discussed below.

First sheet 1 should preferably be attached to first insertion arms 5A and 6A along a line opposite male locking member 10. First sheet 1 may be attached to first insertion arms 5A and 6A by any conventional means, including casting portions of or the ends of the fibers that make up first sheet 1 into insertion arms 5A and 6A, using chemical adhesives to secure the ends of first sheet 1 to insertion arms 5A and 6A, or using mechanical tying devices to physically secure the ends of first sheet 1 to insertion arms 5A and 6A.

The invention also comprises a second sheet 11 having a mouth end 12 and a control end 13 opposite mouth end 12. Second sheet 11 extends between a pair of second insertion arms 5B and 6B. Between second insertion arms 5B and 6B is a second central insertion arm 7B attached to second sheet 11. Second sheet 11, second insertion arms 5B and 6B and second central insertion arm 7B are identical to their counterparts on first sheet 1 in all respects except that second insertion arms are provided with a female locking member 14 along the length of each insertion arm 5B and 6B in a line opposite where sheet 11 attaches to insertion arms 5B and 6B respectively. Another difference is that drawstring 9 and hollow channel 8 need not be included in second insertion arms 5B and 6B, although they may be included if desired.

Female locking member 14 and male locking member 10 are configured to engage one another so that first insertion arms 5A and 6A may be joined with second insertion arms 5B and 6B. This will join first sheet 1 to second sheet 11 and create an elongated hollow member 15 which can be used for gripping the head of fetus. Elongated hollow member 15 should have a mouth appropriately sized to fit over the head of full term human fetus, typically about 10–11 cm in diameter or less.

In a preferred embodiment, one or more end of the first or second insertion arms 5A, 5B, 6A, 6B adjacent control ends 4 and 13 first and second sheets 1 and 11 may be equipped with a notch 16. If a knot is tied in drawstring 9, notch 16 can be used to secure drawstring 9. In another preferred embodiment, the ends of insertions arms 5B, 5B, 6A, and 6B may be provided with a latch or other engaging mechanism suitable for preventing either insertion arm from moving longitudinally relative to each other once they are joined. In yet another preferred embodiment, a pull knob 17A is provided which can be used to gather and secure first sheet 1 near control end 4. A second pull knob 17B may be provided as well which can be used to gather second sheet 11 near control end 13. Alternatively, a single pull knob could be used to gather both sheets 1 and 11 together near their respective control ends. Once the foregoing are gathered into one point, pull knob 17A and/or 17B can be used by the physician or other medical professional to exert force against elongated gripping member 15. Obviously, the medical professional could pull on gripping member 15 without pull knob 17A or 17B, but the likely presence of lubrication on gripping member 15 may make holding onto gripping member 15 easier with pull knob 17A or 17B.

In operation, the physician or other medical professional will usually be presented with the top of the fetus's head at some stage in the birth canal. The physician will insert the first insertion arms 5A and 6A and the first central insertion arm 7A between the fetal head and the birth canal wall until the mouth end 3 of first sheet 1 is positioned below the jaw line of the fetal head. The physician will then engage the second insertion arms 5B and 6B with first insertion arms 5A and 6A and advance the second sheet 11 by sliding second insertion arms 5B and 6B along first insertion arms 6A and 6B. When second insertion arms 5B and 6B encounter the point where the fetal head meets the birth canal wall, the physician will insert second insertion arms 5B and 6B and second central insertion arm 7B between the fetal head and the birth canal wall until the ends of the second insertion arms 5B and 6B are even with the ends of the first insertion arms 5A and 6A or until the fetal head is enclosed within elongated gripping member 15.

Figure 3:
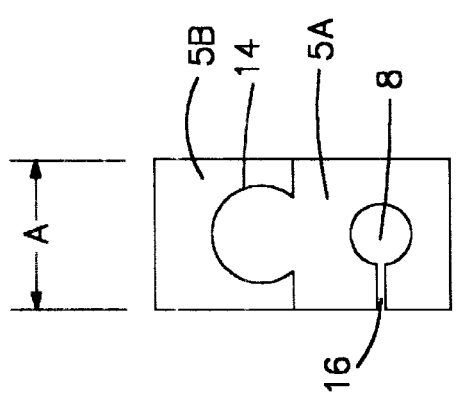
FIG. 3 is an end view of a first insertion arm and a second insertion arm in slidable engagement with each other.

Insertion of elongated gripping member 15 over the fetal head may be facilitated by liberally covering the same with a lubricant such as K-Y JELLY™ and by minimizing the size of first and second insertion arms 5A, 5B, 6A, and 6B and of first and second central insertion arms 7A and 7B. For example, in the preferred embodiment, line A—A in FIG. 3 represents a dimension of between about 5 and about 7 millimeters.

Once elongated gripping member 15 is in place over the fetal head, drawstring 9 is pulled to restrict the size of the mouth of elongated gripping member IS. Drawstring 9 should only be used to tighten the mouth of elongated gripping member 15 slightly so that when traction is applied to elongated gripping member 15, elongated gripping member 15 will not slide forward on the fetal head before compression gripping is initiated. The figures show an exaggerated degree of tightening at the mouth of elongated gripping member 15, for illustrative purposes. Once compression gripping is initiated, tension may be released from drawstring 9, as the compression gripping forces will be sufficient to secure the fetal head in elongated gripping member 15.

At this point, the physician or other medical professional may use the elongated gripping member 15 to apply traction to the fetus. Elongated gripping member 15 will apply the gripping force uniformly to the head of the fetus as traction is applied, thereby lessening the risk of injury or deformity to the fetus.

As stated above, one problem with the prior art is that the close fit between the fetal head and the birth canal walls inhibit the placement of a fabric gripping member 15 around the fetal head. This problem is addressed in the present invention by breaking gripping member 15 into two or more sections (first sheet 1 and second sheet 11 in the preferred embodiment), each comprising only a fraction of the circumference of the whole gripping member 15. Each section may be separately inserted between the fetal head and the birth wall. The shorter length of the leading edge of each section of gripping member 15 makes it easier to get the leading edge of each section around the head of the fetus. However, breaking the gripping member 15 into sections impedes axial gripping, as the fibers cannot extend the full circumference of gripping member 15. Thus, the present invention contemplates using a knit configuration of the fibers in gripping member 15. In this configuration, when longitudinal pressure (away from the fetal head) is applied to the loops, of the knit pattern, they will necessarily become elongated. That is, the loops will be deformed so that their dimension parallel to the longitudinal dimension of gripping member 15 will be elongated. This deformation, in turn, will cause the dimension of the loops perpendicular to the longitudinal dimension of gripping member 15 and parallel to the circumference of gripping member 15 to contract, resulting in a reduction in the circumference of gripping member 15. In this manner, the exertion of longitudinal traction on gripping member 15 will cause gripping member 15 to exert compression gripping uniformly against the fetal head.

It is anticipated that these and other uses and embodiments will be apparent to those skilled in the art in view of the foregoing description and drawings and are intended to be covered by the scope of the following claims.

I claim:

1. A device for assisting in the delivery of a fetus comprising:
   a first sheet comprising a first pair of insertion arms positioned generally parallel to each other, and a plurality of loosely knitted fibers extending between said first pair of insertion arms;
   a second sheet comprising a second pair of insertion arms positioned generally parallel to each other, and a plurality of loosely knitted fibers extending between said second pair of insertion arms;
   wherein said first pair of insertion arms are configured to slidably engage said second pair of insertion arms, whereby said first sheet joined with said second sheet to form an elongated hollow member having a mouth end and a control end opposition said mouth end capable of exerting compression gripping forces against an object placed in said mouth end of said elongated hollow member.

2. A device for assisting in the delivery of a fetus according to claim 1 further comprising a first central arm positioned between and generally parallel to said first pair of insertion arms.

3. A device for assisting in the delivery of a fetus according to claim 2 further comprising a second central arm positioned between and generally parallel to said second pair of insertion arms.

4. A device for assisting in the delivery of a fetus according to claim 1 wherein said mouth of said elongated hollow member is appropriately sized to slide over the head of a full term human fetus.

5. A device for assisting in the delivery of a fetus according to claim 4 further comprising a first central arm positioned between and generally parallel to said first pair of insertion arms.

6. A device for assisting in the delivery of a fetus according to claim 5 further comprising a second central arm positioned between and generally parallel to said second pair of insertion arms.

7. A device for assisting in the delivery of a fetus according to claim 4 further comprising a drawstring positioned in said mouth of said elongated hollow member, whereby said mouth may be tightened to promote the initiation of compression gripping of said fetal head.

8. A device for assisting in the delivery of a fetus according to claim 7 further comprising a first central arm positioned between and generally parallel to said first pair of insertion arms.

9. A device for assisting in the delivery of a fetus according to claim 8 further comprising a second central arm positioned between and generally parallel to said second pair of insertion arms.

10. A device for assisting in the delivery of a fetus according to claim 1 wherein at least some of said fibers are linked together in a jersey knit.

11. A device for assisting in the delivery of a fetus according to claim 10 further comprising a first central arm positioned between and generally parallel to said first pair of insertion arms.

12. A device for assisting in the delivery of a fetus according to claim 11 further comprising a second central arm positioned between and generally parallel to said second pair of insertion arms.

13. A device for assisting in the delivery of a fetus according to claim 10 wherein said mouth of said elongated hollow member is appropriately sized to slide over the head of a full term human fetus.

14. A device for assisting in the delivery of a fetus according to claim 13 further comprising a first central arm positioned between and generally parallel to said first pair of insertion arms.

15. A device for assisting in the delivery of a fetus according to claim 14 further comprising a second central arm positioned between and generally parallel to said second pair of insertion arms.

16. A device for assisting in the delivery of a fetus according to claim 13 further comprising a drawstring positioned in said mouth of said elongated hollow member, whereby said mouth may be tightened to promote the initiation of compression gripping of said fetal head.

17. A device for assisting in the delivery of a fetus according to claim 16 further comprising a first central arm positioned between and generally parallel to said first pair of insertion arms.

18. A device for assisting in the delivery of a fetus according to claim 17 further comprising a second central arm positioned between and generally parallel to said second pair of insertion arms.

19. A device for assisting in the delivery of a fetus according to claim 1 wherein said fibers are monofilament.

* * * * *